(12) United States Patent
Muser

(10) Patent No.: US 6,818,438 B2
(45) Date of Patent: Nov. 16, 2004

(54) CULTURE FLASK

(75) Inventor: Andrew P. Muser, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 15 days.

(21) Appl. No.: 10/674,484

(22) Filed: Sep. 30, 2003

(65) Prior Publication Data
US 2004/0106191 A1 Jun. 3, 2004

Related U.S. Application Data

(60) Provisional application No. 60/416,170, filed on Oct. 4, 2002.

(51) Int. Cl.[7] .............................................. C12M 1/24
(52) U.S. Cl. ................................................... 435/304.3
(58) Field of Search ........................... 435/288.1, 304.1, 435/304.2, 304.3

(56) References Cited

U.S. PATENT DOCUMENTS

| | | |
|---|---|---|
| 491,198 A | 2/1893 | Straus |
| 824,210 A | 6/1906 | Sauer |
| 1,904,222 A | 4/1933 | Halback |
| 2,135,239 A | 11/1938 | Patterson |
| 2,582,398 A | 1/1952 | Siegenthal |
| 2,619,448 A | 11/1952 | Larsen |
| 2,858,036 A | 10/1958 | Earle et al. |
| 2,920,777 A | 1/1960 | Cole |
| 2,947,116 A | 8/1960 | Earle et al. |
| 3,176,879 A | 4/1965 | Mojonnier |
| 3,449,210 A | 6/1969 | Rohde |
| 3,490,501 A | 1/1970 | Manem et al. |
| 3,532,605 A | 10/1970 | Riera |
| 3,589,983 A | 6/1971 | Holderith et al. |
| 3,702,806 A | 11/1972 | Oliva |
| 3,726,764 A | 4/1973 | House et al. |
| 3,853,712 A | 12/1974 | Froman et al. |
| 3,870,602 A * | 3/1975 | Froman et al. .......... 435/304.3 |
| 4,073,695 A | 2/1978 | Lyman |
| 4,121,976 A | 10/1978 | Gleeson |
| 4,144,136 A | 3/1979 | Corbeil |
| 4,296,205 A | 10/1981 | Verma |
| 4,334,028 A | 6/1982 | Carver |
| D272,602 S | 2/1984 | Gregory |
| 4,534,483 A | 8/1985 | Kassis et al. |
| 4,640,895 A | 2/1987 | Davis |
| 4,734,373 A | 3/1988 | Bartal |
| 4,769,858 A | 9/1988 | Gamm et al. |
| 4,770,854 A * | 9/1988 | Lyman ....................... 422/102 |
| 4,851,351 A | 7/1989 | Akamine |
| 4,902,286 A | 2/1990 | Ranoux |
| 4,912,048 A | 3/1990 | Smith et al. |
| 4,927,764 A * | 5/1990 | Lyman et al. ............ 435/304.3 |
| 4,935,371 A | 6/1990 | Rickloff |
| 4,968,623 A | 11/1990 | Franks |
| 5,002,199 A | 3/1991 | Frahm |
| 5,047,347 A | 9/1991 | Cline |
| 5,084,393 A | 1/1992 | Rogalsky |
| 5,112,957 A | 5/1992 | Pollard |
| 5,139,952 A | 8/1992 | Honda et al. |

(List continued on next page.)

FOREIGN PATENT DOCUMENTS

WO    WO 96/00780    1/1996

*Primary Examiner*—David A. Redding

(57) ABSTRACT

A tissue culture flask includes a base, a cover and a cap. The base has a bottom wall and a ramp extending up at an obtuse angle from the bottom wall to the front end of the flask. The flask also includes a sidewall enclosure that extends up from the bottom wall and the ramp. The sidewall enclosure includes a front wall at the end of the ramp furthest from the bottom wall. The front wall includes an opening, and a substantially tubular neck extends forward from the opening. The neck has a substantially circular cross-section at the front end. However, portions of the neck at the rear end have a substantially circular cross-section across the top of the neck and a substantially elliptical cross-section across the bottom of the neck. The elliptical sections of the neck are substantially tangent to the ramp at the front wall of the flask. The geometry facilitates access by pipettes, scrapers and other instruments.

17 Claims, 4 Drawing Sheets

U.S. PATENT DOCUMENTS

| | | |
|---|---|---|
| 5,151,366 A | 9/1992 | Serkes et al. |
| 5,210,038 A | 5/1993 | Jaeger et al. |
| 5,262,326 A | 11/1993 | Jaeger et al. |
| 5,272,084 A | 12/1993 | O'Connell et al. |
| 5,310,658 A | 5/1994 | Berndt |
| 5,310,676 A | 5/1994 | Johansson et al. |
| 5,391,496 A | 2/1995 | Kayal et al. |
| 5,462,874 A | 10/1995 | Wolf et al. |
| 5,482,854 A | 1/1996 | O'Leary et al. |
| 5,565,353 A | 10/1996 | Klebe et al. |
| 5,570,802 A | 11/1996 | Wang et al. |
| 5,578,491 A | 11/1996 | Kayal et al. |
| 5,595,907 A | 1/1997 | Kayal et al. |
| 5,618,731 A | 4/1997 | Stevens et al. |
| 5,622,865 A | 4/1997 | Kayal et al. |
| D379,520 S | 5/1997 | Stevens et al. |
| D379,521 S | 5/1997 | Stevens et al. |
| 5,672,505 A | 9/1997 | Jones et al. |
| 5,693,537 A | 12/1997 | Wilson et al. |
| 5,695,987 A | 12/1997 | Kayal et al. |
| 5,716,798 A | 2/1998 | Monthony et al. |
| 5,763,275 A | 6/1998 | Nagels et al. |
| 5,766,936 A | 6/1998 | Kayal et al. |
| 5,783,440 A | 7/1998 | Stevens |
| 5,801,054 A | 9/1998 | Kiel et al. |
| 5,858,310 A | 1/1999 | Jackson et al. |
| 5,924,583 A | 7/1999 | Stevens et al. |
| 5,935,845 A | 8/1999 | Koontz |
| 5,939,314 A | 8/1999 | Koontz |
| 6,056,924 A | 5/2000 | Jackson et al. |
| 6,095,356 A | 8/2000 | Rits |
| 6,114,165 A | 9/2000 | Cai et al. |
| 6,150,159 A | 11/2000 | Fry |
| 6,210,959 B1 | 4/2001 | Lodri et al. |

* cited by examiner

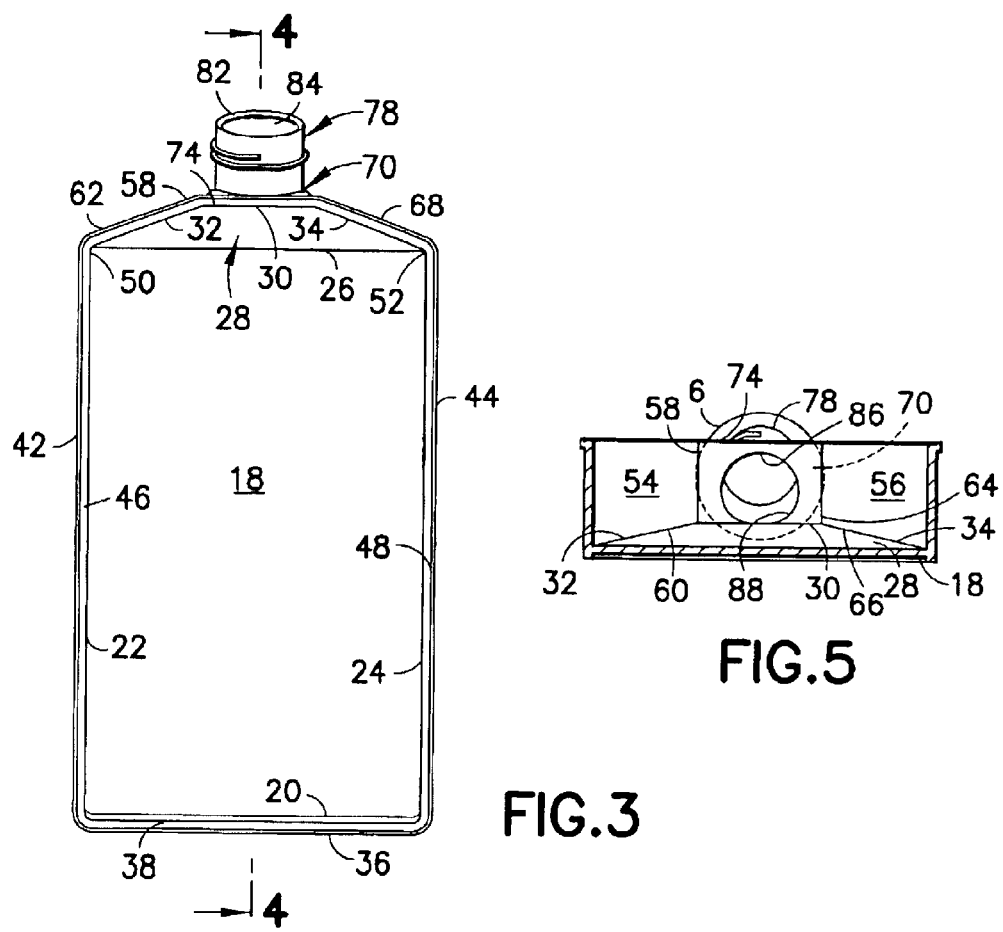
FIG. 3
FIG. 5
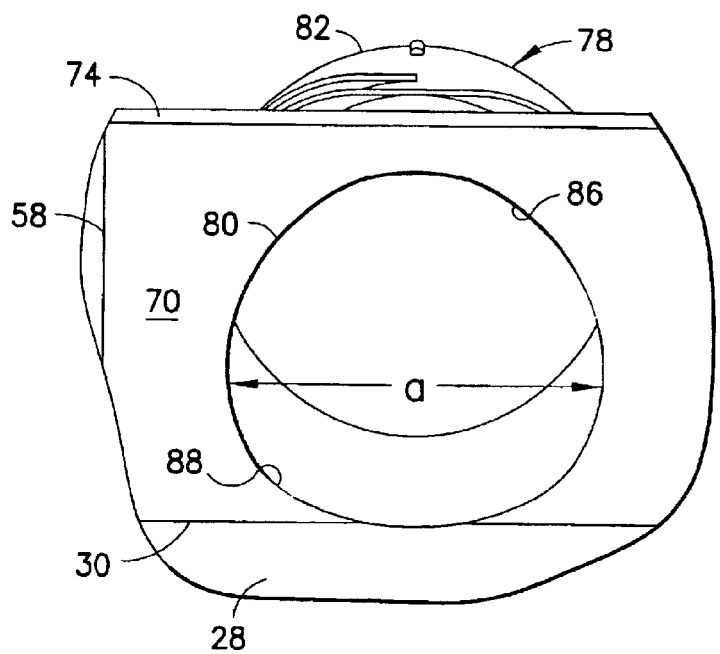
FIG. 6 ial Application 60/416,170 filed on Oct. 4, 2002.

CULTURE FLASK

This application claims benefit to U.S. Provisional Application 60/416,170 filed on Oct. 4, 2002.

BACKGROUND OF THE INVENTION

1. Field of the Invention

The present invention relates generally to laboratory flasks. More particularly the present invention relates to improvements in flasks for growing cells, microorganisms and tissue in a culture medium.

2. Description of the Related Art

Tissue culture flasks are widely used in the laboratory for many purposes. Typically, these flasks are used to culture microorganisms or tissues in a culture medium or agar which is adhered to an interior surface of the flask. The tissues are introduced into the flask through a capped opening. The flask is re-capped and inserted into a stacking facility or chamber, such as an oven, to facilitate the growth of the microorganisms in the medium. In laboratory practice, it is quite common to arrange or stack several tissue culture flasks in a single chamber. Thus, the size of the individual flasks becomes a concern as it is desirable to position as many flasks as possible in a single chamber.

Another concern in constructing tissue culture flasks is the volume within the flask which is available for accommodation of both the culture medium as well as the tissue. In order to enhance stackability of the flasks in the chamber, many tissue culture flasks are generally flat rectangular containers having a neck or opening at one end wall permitting access to the interior of the flask. The flask may be filled with culture medium and tissue to a level approaching the bottom of the neck or opening. Thus, the usable volume of the flask is determined by the vertical distance between the bottom wall of the flask and the flask opening, since the culture medium and tissue cannot extend above the flask opening. Spacing the opening from the bottom wall of the flask increases the usable volume of the flask, but also increases the overall stacked height of the flask. Thus, fewer flasks can be stacked in a chamber. The size of the opening of the flask can be decreased to increase the usable volume. However, a smaller opening limits accessibility to the entire bottom wall of the flask. This reduced accessibility creates problems, particularly in those situations where it is necessary to access the tissue growing in the medium on the bottom wall of the flask. An optimal flask would permit the user to access the entire bottom surface of the flask, including the corners, with a scraper, pipette or other instrument.

It is therefore desirable to provide a tissue culture flask having a sufficiently large opening so as to permit access to the entire bottom surface thereof without decreasing the usable volume or increasing the stacked height of the flask.

It is another object of the present invention to provide an improved laboratory flask for the culturing of microorganisms, cells and tissues.

It is a further object of the present invention to provide a tissue culture flask which permits access to the interior of the flask through an opening therein.

It is still a further object of the present invention to provide a tissue culture flask of minimal stacked height which maximizes the usable volume for culture medium and tissue.

SUMMARY OF THE INVENTION

The invention is a laboratory flask including a planar bottom wall and a planar ramp extending up from the bottom wall. The ramp defines an acute angle incline with respect to the planar bottom wall. The flask further includes a plurality of interconnected sidewalls extending up from the bottom wall and the ramp for defining an enclosure about the bottom wall and the ramp. The sidewalls preferably are aligned substantially perpendicular to the plane of the bottom wall. A top wall or cover extends across portions of the sidewalls remote from the bottom wall and the ramp. The top wall is substantially planar and substantially parallel to the bottom wall to facilitate stacking of a plurality of flasks.

Access to the interior of the flask is achieved by an elongate hollow neck that projects from a sidewall that intersects an area of the ramp furthest from the planar bottom wall. The hollow neck has a central axis aligned at an acute angle to the bottom wall, and preferably at an acute angle that is less than the angle between the ramp and the bottom wall. Exterior portions of the hollow neck may be substantially cylindrical at locations spaced from the sidewalls and may have an array of external threads at the end of the neck spaced from the sidewalls of the flask.

The interior of the hollow neck is not uniformly cylindrical along the length of the neck. More particularly, the interior of the neck may be cylindrical with a substantially constant internal diameter at locations adjacent the threaded end of the neck. However, a slight tapering consistent with molding techniques may be required. Interior portions of the neck adjacent the sidewalls of the flask are not cylindrical, and define a combination of a circular and elliptical sections at the opening adjacent the sidewall. In particular, the upper half of the opening adjacent the sidewall of the neck may be generally circularly generated. However, the lower half of the interior of the hollow neck adjacent the sidewall are generally elliptical, with the major axis of the ellipse being substantially parallel to the bottom wall. The elliptical bottom half of the interior of the neck adjacent the sidewall of the flask may be substantially tangent to the planar ramp.

Interior portions of the hollow neck then gradually change in cross-section between the externally threaded end of the neck and the opening in the sidewall that communicates with the interior of the flask. In view of this geometry, a line extending along the low points of the interior of the hollow neck defines an angle with respect to the planar bottom wall that is less than the angle defined by both the ramp and the central axis of the hollow neck. The geometry of the interior of the hollow neck relative to the ramp and the bottom wall ensures that the neck opening is above the media level and reduces the risk of contamination in the flask. Additionally, the geometry of the interior of the neck allows for sufficient and efficient access by pipettes, scraper or other instruments.

DESCRIPTION OF THE DRAWINGS

FIG. 3 is a top plan view of the base.

FIG. 5 is a cross-sectional view taken along line 5-5 in FIG. 4.

FIG. 6 is a cross-sectional view similar to FIG. 5, but showing an enlarged area of the flask adjacent the neck.

DETAILED DESCRIPTION

Figure 1:
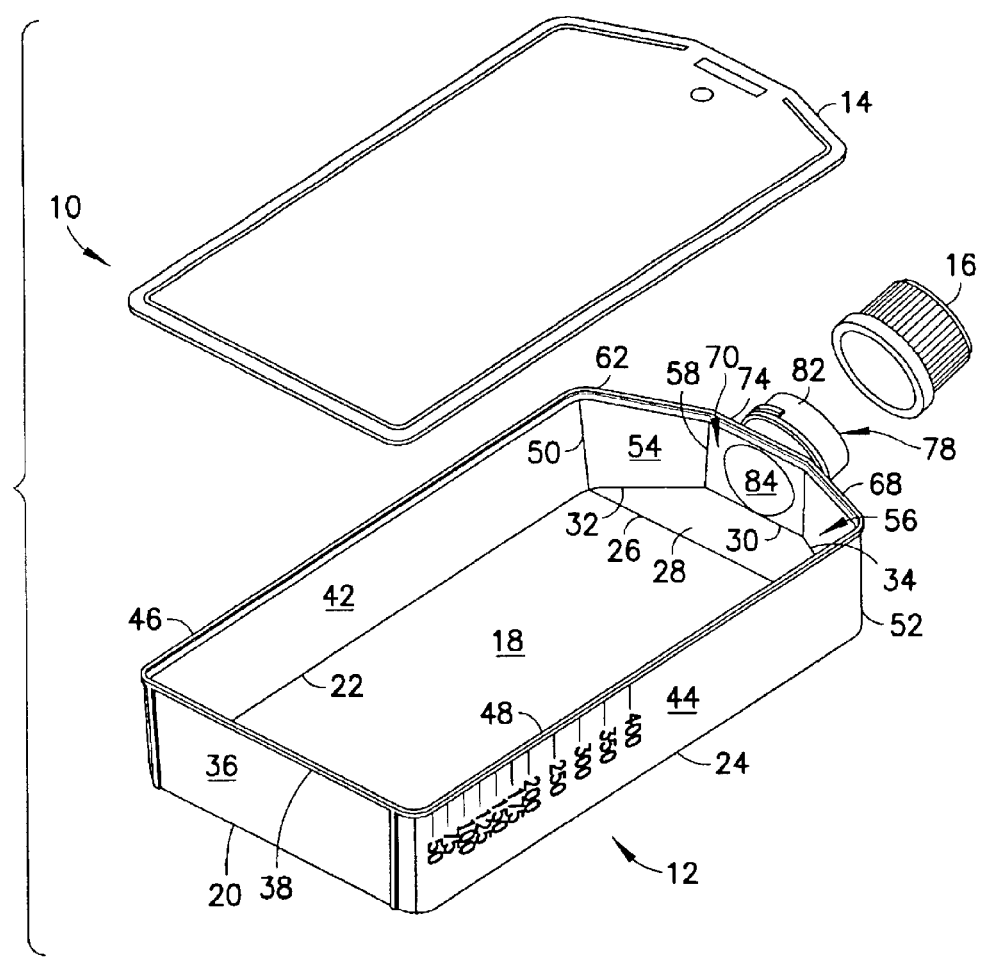
FIG. 1 is an exploded perspective view of a flask in accordance with the subject invention.
Figure 2:
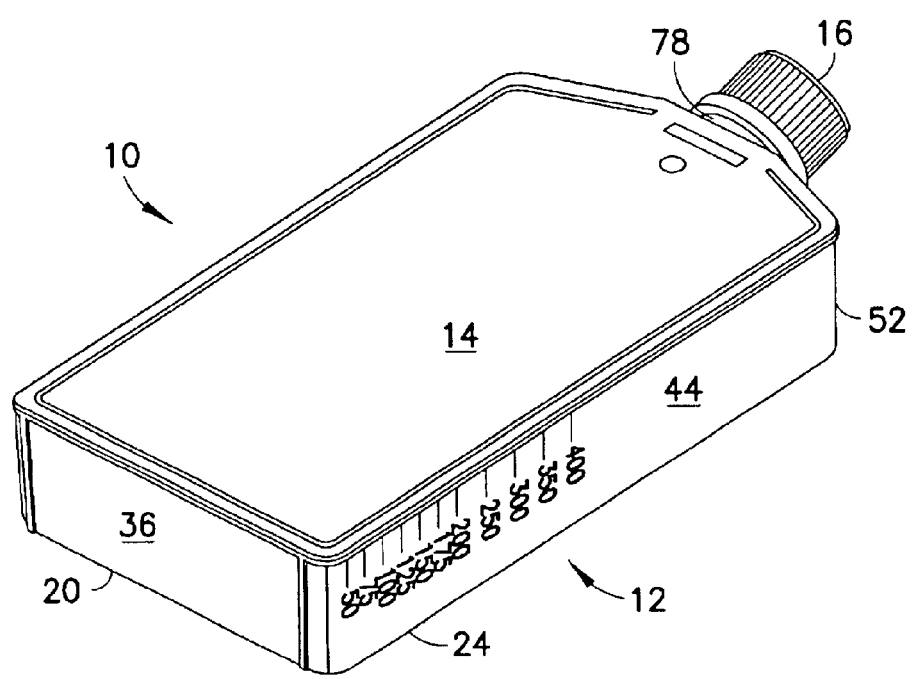
FIG. 2 is a perspective view of the flask of FIG. 1 in the fully assembled condition.
Figure 4:
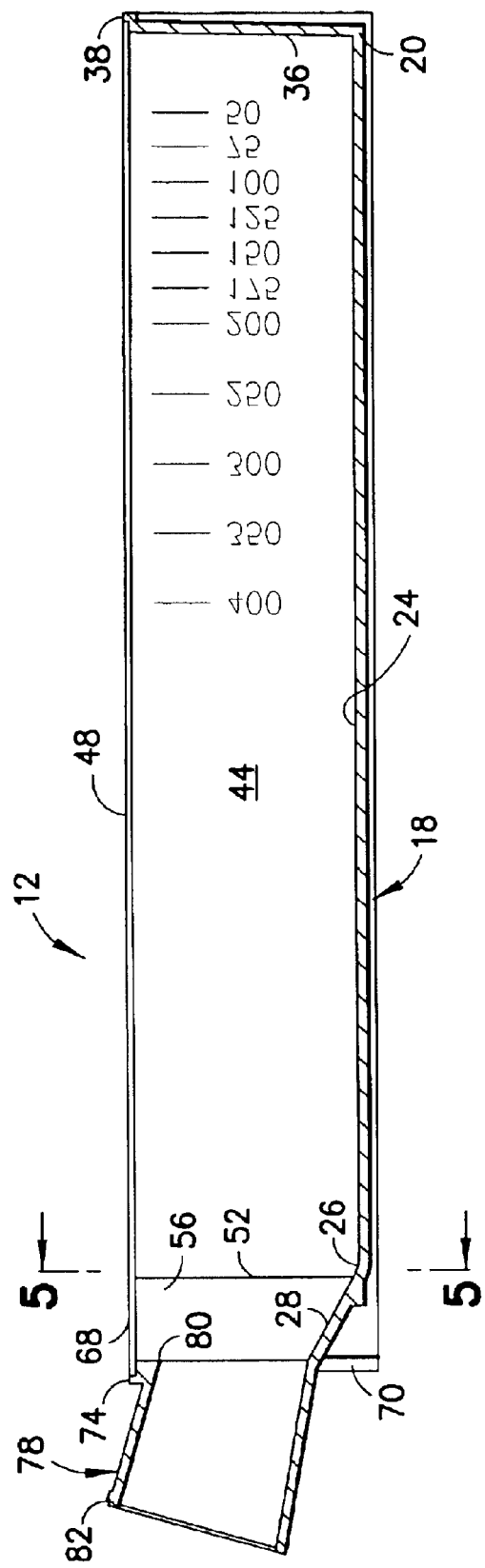
FIG. 4 is a cross-sectional view taken along line 4-4 in FIG. 3.

A tissue culture flask in accordance with the subject invention is identified generally by the numeral 10 in FIGS.

1–7. Tissue culture flask 10 is a generally hexagonal container formed from a base 12, a cover 14 and a cap 16. Base 12 is unitarily formed from a plastic material, and preferably a polystyrene. Base 12 includes a substantially planar rectangular bottom wall 18 with a back end 20, first and second sides 22 and 24 and a front end 26. A substantially planar isosceles trapezoidal ramp 28 extends unitarily from front end 26 of bottom wall 18 and is aligned to bottom wall 18 at an obtuse angle of about 150°. Hence, the plane of trapezoidal ramp 28 defines an incline of about 30° when bottom wall 18 is supported on a horizontal surface. Front end 26 of bottom wall 18 defines the longer of two parallel bases for trapezoidal ramp 28. Ramp 28 further includes a shorter parallel base end 30 and first and second equal sides 32 and 34 that converge from end 26 toward end 30.

Base 12 of flask 10 includes a substantially rectangular back wall 36 that projects orthogonally from bottom wall 18 at a location adjacent back end 20 of bottom wall 18. Back wall 36 includes a top edge 38 aligned substantially parallel to bottom wall 18. Base 12 also includes first and second substantially parallel rectangular sidewalls 42 and 44 that extend orthogonally from bottom wall 18 at locations adjacent first and second sides 22 and 24 respectively. First and second sidewalls 42 and 44 include top edges 46 and 48 respectively that are parallel to bottom wall 18 and substantially coplanar with top edge 38 of back wall 36. Sidewalls 42 and 44 have front ends 50 and 52 substantially aligned with opposed ends of front end 26 of bottom wall 18.

Base 12 further includes first and second substantially planar transition walls 54 and 56 that converge toward one another from front ends 50 and 52 of first and second sidewalls 42 and 44 respectively. First transition wall 54 is substantially rectangular and has a rear end 50 coincident with front end 50 of first sidewall and a front end 58 substantially aligned with and orthogonal to front end 30 of ramp 28. First transition wall 54 further includes a bottom edge 60 that is substantially coplanar with bottom wall 18 and a top edge 62 that is substantially in the plane defined by top edges 38, 46 and 48. Ramp 28 intersects rectangular first transition wall 54 at an angle to the parallel top and bottom edges 60 and 62 thereof. In a similar manner, second transition wall 56 is substantially rectangular and is aligned substantially orthogonal to the plane defined by bottom wall 18. Second transition wall 56 further includes a rear end 52 coincident with the front end 52 of second sidewall 44 and a front end 64 substantially aligned with and orthogonal to front end 30 of ramp 28. Second transition wall 56 is defined further by a bottom edge 66 aligned parallel to the plane of bottom wall 18 and a top edge 68 substantially in the plane defined by top edges 38, 46, 48 and 62. Ramp 28 intersects second transition wall 56 at side edge 34 of ramp 28 and at an angle to bottom edge 66 of second transition wall 56.

Base 12 of flask 10 further includes a substantially planar front wall 70 aligned substantially orthogonal to the plane defined by bottom wall 18. Front wall 70 is substantially rectangular and has first and second sides 58 and 64 coincident with the front ends of first and second transition walls 54 and 56 respectively. Front wall 70 further includes a top edge 74 that extends between top edges 62 and 68 of first and second transition walls 54 and 56. Top edge 74 lies in the plane defined by top edges 38, 46, 48, 62 and 68.

Base 12 of flask 10 further includes a generally tubular neck 78 that extends forwardly from front wall 70. Neck 78 includes an open rear end 80 at front wall 70 that communicates with the region of base 12 above bottom wall 18 and ramp 28. Neck 78 further includes a front end 82 and a tubular passage 84 extending between rear end 80 and front end 82. Portions of neck 78 adjacent front end 82 are substantially cylindrically generated and exterior regions of neck 78 adjacent front end 82 include an array of external threads for threaded engagement of cap 16. Neck 78 includes a central axis aligned to the plane of bottom wall 18 at an angle of about 15°. Neck 78 is not cylindrically generated about axis A. Rather, rear end 80 of neck 78 is defined by a continuous compound curve with a circularly generated top section 86 and an elliptically generated bottom section 88. Sections of neck 78 between rear end 80 and front end 82 gradually transition between the circular cross-section adjacent front end 82 and the compound curved section adjacent rear end 80. The minimum or vertical dimension of the rear opening 80 of neck 78 is about 90% of the maximum or width dimension of the opening 80. The maximum inside dimension or width "a" of the opening 80 at the rear end of neck 78 is about 97% of the inside diameter of neck 78 at front end 82. The slightly smaller inside width dimension at rear opening 80 of neck 78 is intended to facilitate mold removal. Elliptically generated portion 88 of rear end 80 of neck 78 is substantially tangent to front edge 30 of ramp 28. However, the line connecting the low point of rear end 80 of neck 78 with the low point of front end 82 of neck 78 is aligned at an angle of about only 10° to the plane of bottom wall 18. The highest inwardly facing point on circular portion 86 of rear end 80 of neck 78 is displaced bellow top edge 74 of front wall 70 by a distance that represents approximately 16% of the total height of the front wall. Thus, the exterior of neck 78 is displaced below top edge 74 of front wall 70 by a distance approximately equal to 5.5% of the total height of front wall 70.

Cover 14 of flask 10 is substantially planar and defines a hexagon with a shape that permits cover 14 to rest on top edges 38, 46, 48, 62, 68, and 74 of base 12 or to nest slightly with the vertical walls of base 12. Cover 14 may be secured in position on base 12 by appropriate application of adhesive or by a known bonding technique, such as ultrasonic welding.

Flask 10 can be used to contain a culture medium and tissue that will adhere to the interior surface of the bottom wall. Flask 10 then is inserted into an environmental chamber, such as an oven to facilitate the growth of microorganisms. Periodically, the flask may be removed from the environmental chamber and opened to permit removal of sample microorganisms with a pipette or other similar instrument. The geometry of neck 78 allows the rear end opening 80 of neck 78 to be above the level of media in flask 10, and hence reduces the risk of contamination in flask 10. This geometry of neck 78 allows for access by pipettes and scrapers while facilitating ease of pouring to all interior corners of flask. The geometry also allows cap 16 to seal against front end 82 of neck 78, while preventing collection of media in neck 78 and minimizing risks for contamination in neck 78.

What is claimed is:

1. A tissue culture flask comprising a bottom wall, a ramp extending up from said bottom wall at an obtuse angle, said ramp having a front end at a portion of said ramp furthest from said bottom wall, a sidewall enclosure extending up from said bottom wall and said ramp, a cover extending across said sidewall enclosure in opposed spaced relationship to said bottom wall and said ramp, said sidewall enclosure including a front wall panel extending up from said front end of said ramp, said front wall having an opening formed therethrough, a substantially tubular neck extending outwardly from said front wall at said opening for providing communication to portions of said flask bounded by said sidewall enclosure, portions of said tubular neck adjacent said opening in said front wall defining an upwardly concave elliptical arc and a downwardly concave circular arc.

2. The tissue culture flask of claim 1, wherein said elliptical arc of said opening in the front wall defines a major axis extending parallel to said bottom wall.

3. The tissue culture flask of claim 2, wherein said elliptical arc of said opening in said front wall is substantially tangent to said front end of said ramp.

4. The tissue culture flask of claim 2, wherein said circular arc of said opening in said front wall has a diameter coincident with said major axis of said elliptical arc.

5. The tissue culture flask of claim 1, wherein said sidewall enclosure has a top edge secured to said cover, said opening in said front wall being spaced below said top edge of said sidewall enclosure.

6. The tissue culture flask of claim 1, wherein said neck has a front end with a substantially circular cross-section.

7. The tissue culture flask of claim 6, wherein said neck has an array of external threads in proximity to said front end of said neck, said tissue culture flask further comprising a cap threadedly engaged with said threads on said neck.

8. The tissue culture flask of claim 1, wherein said cover is substantially parallel to said bottom wall.

9. The tissue culture flask of claim 1, wherein said bottom wall and said ramp each are substantially planar.

10. The tissue culture flask of claim 9, wherein said ramp is aligned to said bottom wall at an angle of about 150°.

11. The tissue culture flask of claim 10, wherein said neck has a neck axis aligned to the bottom wall at an angle of about 15°.

12. The tissue culture flask of claim 11, wherein a plane passing vertically and symmetrically through said neck intersects said neck along a bottom extreme of said neck, said bottom extreme defining a line aligned to the bottom wall at an angle of approximately 10°.

13. A tissue culture flask having a base unitarily molded from a plastic material, said base comprising a substantially rectangular bottom wall having opposite front and rear ends and opposed sides, a substantially planar isosceles trapezoidal ramp extending from said front end of said bottom wall and aligned to said bottom wall at an obtuse angle, said ramp having a front end parallel to said front end of said bottom wall and first and second sides converging from said bottom wall toward said front end of said ramp, a back wall extending up from said back end of said bottom wall, first and second sidewalls extending up from said first and second sides of said bottom wall, first and second transition walls extending up from said first and second converging sides of said ramp and a front wall extending up from said front end of said ramp, said front wall having an opening formed therethrough and a substantially tubular neck extending out from said opening in said front wall, said tubular neck having a passage extending therethrough and into said flask, portions of said tubular neck at said opening in said front wall having an elliptically generated upwardly concave surface substantially tangent to said front end of said ramp, said tissue culture flask further having a cover secured to said back wall, said front wall, said sidewalls and said transition walls in opposed spaced relationship to said bottom wall and said ramp.

14. The tissue culture flask of claim 13, wherein the opening and the neck are spaced from the cover.

15. The tissue culture flask of claim 13, wherein portions of said neck adjacent said front wall include a downwardly concave circularly generated portion joined continuously with said upwardly concave elliptically generated portion.

16. The tissue culture flask of claim 15, wherein said neck has front end spaced outwardly from said front wall, portions of said neck adjacent said front end being substantially cylindrically generated and having means formed thereon for releasably engaging a cap.

17. The tissue culture flask of claim 13, wherein the ramp is aligned to the bottom wall at an obtuse angle of about 150°.

* * * * *